(12) United States Patent
Komatsubara (10) Patent No.: US 10,863,722 B2
(45) Date of Patent: Dec. 15, 2020

(54) ABSORBENT ARTICLE FOR PET ANIMALS

(71) Applicant: UNICHARM CORPORATION, Shikokuchuo-shi, Ehime (JP)

(72) Inventor: Daisuke Komatsubara, Kanonji (JP)

(73) Assignee: UNICHARM CORPORATION, Ehime (JP)

(*) Notice: Subject to any disclaimer, the term of this patent is extended or adjusted under 35 U.S.C. 154(b) by 183 days.

(21) Appl. No.: 15/757,311

(22) PCT Filed: Jun. 16, 2016

(86) PCT No.: PCT/JP2016/067955
§ 371 (c)(1),
(2) Date: Mar. 2, 2018

(87) PCT Pub. No.: WO2017/038204
PCT Pub. Date: Mar. 9, 2017

(65) Prior Publication Data
US 2019/0069522 A1    Mar. 7, 2019

(30) Foreign Application Priority Data
Sep. 3, 2015    (JP) .................. 2015-174033

(51) Int. Cl.
*A01K 23/00*    (2006.01)
*A61F 13/15*    (2006.01)

(52) U.S. Cl.
CPC .............. *A01K 23/00* (2013.01); *A61F 13/15* (2013.01); *A61F 2013/15186* (2013.01)

(58) Field of Classification Search
CPC ............... A01K 23/00; A61F 13/15; A61F 2013/15186

(Continued)

(56) References Cited

U.S. PATENT DOCUMENTS 4,996,949 A * 3/1991 Wunderman .......... A01K 23/00
                                                        119/850
8,092,630 B2 * 1/2012 Ikegami ................ A01K 23/00
                                                        156/250

(Continued)

FOREIGN PATENT DOCUMENTS

CA    2831539 A1 * 10/2012 ............. A01K 23/00
CA    2831541 A1 * 10/2012 ............. A01K 23/00

(Continued)

OTHER PUBLICATIONS

International Search Report in PCT Application No. PCT/JP2016/067955, dated Sep. 20, 2016, 2pp.

*Primary Examiner* — Monica L Barlow
*Assistant Examiner* — Aaron M Rodziwicz
(74) *Attorney, Agent, or Firm* — Hauptman Ham, LLP (57) ABSTRACT

Provided is an absorbent article suitable for bedridden pet animals.
An absorbent article (10) for pet animals has a longitudinal direction (Y) and a width direction (X) crossing each other and includes: a body-facing surface and a non-body-facing surface opposite to each other; a first edge and a second edge (10a, 10b) opposite to each other in the longitudinal direction (Y); a tail facing area (13) facing a tail of the pet (5); a first section (11) extending from the tail facing area (13) toward the first edge (10a) and covering one of buttocks of the pet (5); a second section (12) extending from the tail facing area (13) toward the second edge (12b) and covering another one of the buttocks of the pet (5); an absorbent core (15) positioned between the first section (11) and the second section (12); and an attachment (21) positioned on the first section (11) and capable of attaching to an attachment target part (22) on the second section (12).

1 Claim, 8 Drawing Sheets

(58) Field of Classification Search
USPC .......................................... 119/867, 868, 869
See application file for complete search history.

(56) References Cited

U.S. PATENT DOCUMENTS

| | | | | |
|---|---|---|---|---|
| 8,161,916 B2* | 4/2012 | Bertocci | ................... | A61D 9/00 |
| | | | | 119/850 |
| 2007/0129702 A1* | 6/2007 | Gribben | ................. | A01K 23/00 |
| | | | | 604/392 |
| 2011/0209675 A1* | 9/2011 | Esperon | ................. | A01K 23/00 |
| | | | | 119/868 |
| 2014/0165926 A1* | 6/2014 | Marks | .................... | A01K 23/00 |
| | | | | 119/838 |
| 2015/0045762 A1* | 2/2015 | Komatsubara | ......... | A01K 23/00 |
| | | | | 604/385.201 |

FOREIGN PATENT DOCUMENTS

| | | | | | |
|---|---|---|---|---|---|
| CA | | 2831734 A1 | * | 10/2012 | ............ A01K 23/00 |
| CA | | 2831774 A1 | * | 10/2012 | ............ A01K 23/00 |
| CA | | 2831778 A1 | * | 10/2012 | ............ A01K 23/00 |
| JP | | 2004-159591 A | | 6/2004 | |
| JP | | 2004-159592 A | | 6/2004 | |
| JP | | 2012-187095 A | | 10/2012 | |
| JP | | 2013-46587 A | | 3/2013 | |
| WO | WO-2012164961 A1 | | * | 12/2012 | ............ A01K 23/00 |
| WO | WO-2012164962 A1 | | * | 12/2012 | ............ A01K 23/00 |
| WO | WO-2012172806 A1 | | * | 12/2012 | ............ A01K 23/00 |
| WO | WO-2012172874 A1 | | * | 12/2012 | ............ A01K 23/00 |

* cited by examiner

ABSORBENT ARTICLE FOR PET ANIMALS

RELATED APPLICATIONS

The present application is a National Phase of PCT/JP2016/067955, filed Jun. 16, 2016, and claims priority based on Japanese Patent Application No. 2015-174033, filed Sep. 3, 2015.

TECHNICAL FIELD

The present disclosure relates to an absorbent article that absorbs excretion from pet animals such as cats and dogs.

BACKGROUND ART

Absorbent articles worn on the body of pet animals such as cats and dogs have conventionally been known. Patent Literature 1 discloses one example of such an absorbent article for pet animals. Specifically, the absorbent article includes a ventral area, a dorsal area, an intermediate area between the dorsal area and the ventral area, a liquid-permeable interior layer sheet, a liquid-impermeable exterior layer sheet, and an absorbent core interposed between the interior and exterior layer sheets.

Patent Literature 2 discloses another absorbent article for pet animals that includes a liquid-permeable interior layer sheet, a liquid-impermeable exterior layer sheet, and an absorbent core interposed between the interior and exterior sheets. This article is worn by being encircled around the body of a pet animal.

CITATION LIST

Patent Literature

PTL 1: Japanese Unexamined Patent Application Publication No. 2004-159591 (JP2004-159591A)
PTL 2: Japanese Unexamined Patent Application Publication No. 2012-187095 (JP2012-187095A)

SUMMARY OF INVENTION

Technical Problem

The absorbent article for pet animals disclosed in Patent Literature 1 is mainly for female pet animals. The article is worn on the body of a pet, while covering the excretory opening (vulva), by connecting the ventral area and the dorsal area to each other with both curved side edges of the intermediate area conforming to and fit the hind legs. Thus, the excretion can be prevented from leaking.

The absorbent article for pet animals disclosed in Patent Literature 2 is mainly for male pet animals. The article can be worn, while covering the excretory opening, with both end portions of the article, encircled around the waist, attached to each other, and whereby the excretion can be prevented from leaking out.

A relatively old (10 to 20 years old) pet is likely to be bedridden to have one of left and right sides of its body constantly in contact with a floor surface. The pet having kept lying on one side for a relatively long period of time might have a bedsore. The bedsore is likely to occur when pressure is applied to a part of the body that has become damp. In this context, the absorbent article worn on an elderly pet has a risk that an inner portion might become damp to be in a wet state, which is likely to lead to a bedsore, due to the excretion. To prevent the inner portion from becoming damp, an absorbent sheet may be provided on a floor instead of making the pet wear the absorbent material. However, this results in the body of the pet being soiled by the excretion. Furthermore, the excretion might spread outward beyond the absorbent sheet to be on the floor.

Some bedridden pet animals are still capable of moving their legs. The absorbent article not stably attached to the body of such a pet might be detached due to the movement of the legs, and thus fail to absorb bodily fluid.

The present invention is directed to an improvement of the conventional absorbent articles for pet animals, and an object of the present invention is to provide an absorbent article suitable for bedridden pet animals.

Solution to Problem

The present invention for solving the problems described above is directed to an absorbent article for pet animals having a longitudinal direction and a transverse direction crossing each other and including: a body-facing surface and a non-body-facing surface opposite to each other; a first edge and a second edge opposite to each other in the longitudinal direction; a tail facing area facing a tail of a pet; a first section extending from the tail facing area toward the first edge and covering one of the buttocks of the pet; a second section extending from the tail facing area toward the second edge and covering another one of the buttocks of the pet; an absorbent core positioned between the first and second sections; and a fastener positioned on the first section and capable of fastening target part on the second section.

An attachment is positioned on a non-body-facing surface of the first section and an attachment target part is positioned on a body-facing surface of the second section. Thus, the first section and the second section can be connected to each other, and the absorbent article should not come unfastened from the body owing to the movement of the legs.

The fastener is positioned on a body-facing surface of the first section and the attachment target part is positioned on the body-facing surface or the non-body-facing surface of the second section. The first section and the second section have end portions connected to each other while being overlapped with each other or facing each other.

The absorbent article further includes a tape fastener including: a fixed portion fixed to the first section; and a free portion extending outward from the first edge in the longitudinal direction and capable of being attached to the second section, and the attachment positioned on the free portion. Thus, the article can be put on a pet with a relatively large body. Furthermore, the tape fastener can be used for a tape used for disposal of the article.

The absorbent article further has a first axis bisecting a length of the absorbent article in the width direction, and the attachment is positioned on the first axis on the first section. Thus, the first and the second sections may be connected to each other in a well-balanced manner.

The absorbent article further has a first axis bisecting a length of the absorbent article in the width direction, and further includes both side areas positioned more on an outer side than both side edges of the absorbent core in the width direction and extend in the longitudinal direction, and the tail facing area is positioned on one of the side areas. Thus, a putting operation can be smoothly performed with the tail stably attached to the tail facing area.

The attachment is positioned between the one of the side areas and the first axis. Thus, the one of the side areas provided with the tail facing area can be pulled and attached to the other one of the side areas. This improves fittability to the body.

A first elastic member extending in the longitudinal direction is provided on another one of the both side areas. Thus, the other one of the side areas is fit around the legs.

The one side areas provided with the tail facing area is further provided with a second elastic member extending in the longitudinal direction. This improves fittability on the back.

The one side portion extends diagonally downward relative to a body of the pet, when the absorbent article is in a worn state. Thus, a portion of the body covered with the absorbent article is small. Thus, the inner portion of the absorbent article can be prevented from becoming damp.

Advantageous Effects of Invention

The absorbent article for pet animals according to one or more of embodiments according to the present invention includes the tail facing area facing the tail of the pet and the first section and the second section covering the buttocks. This article can quickly absorb a relatively large amount of excretion, flowed toward the floor surface, with the absorbent core while a bedridden pet is lying on one side. Thus, an inner portion of the article can be prevented from becoming damp and the pet can be prevented from having a bedsore. The first section and the second section can be detachable attached to each other with the attachment. This improves fittability around the legs.

BRIEF DESCRIPTION OF DRAWINGS

The drawings illustrate specific embodiments of the present invention, including optional and preferred embodiments as well as essential features of the invention.

DESCRIPTION OF EMBODIMENTS

The embodiments described below relate to an absorbent article for pet animals illustrated in FIG. 1 to FIG. 8, including both optional and preferred features as well as those features which are essential features of the present invention.

As illustrated in FIG. 1 to FIG. 4, an absorbent article 10 for pet animals has a longitudinal direction Y and a width direction X that cross each other, a first axis P bisecting a length in the width X, and a second axis Q bisecting a length in the longitudinal direction Y, and includes a body-facing surface facing the body of a pet 5, and a non-body-facing surface opposite to the body-facing surface. The absorbent article 10 has a rectangular shape, elongated in the longitudinal direction Y, defined by first and second edges 10a and 10b and both side edges 10c and 10d in between the edges. The first and the second edges 10a and 10b are opposed to each other in the longitudinal direction Y and the both side edges 10c and 10d extend along the longitudinal direction Y.

The absorbent article 10 includes a tail facing area 13 to face the tail of the pet 5, a first section 11 extending from the tail facing area 13 towards the first edge 10a and covers one of the buttocks of the pet 5, and a second section 12 extending from the tail facing area 13 towards the second edge 10b and covers the other one of the buttocks of the pet 5.

Figure 3:
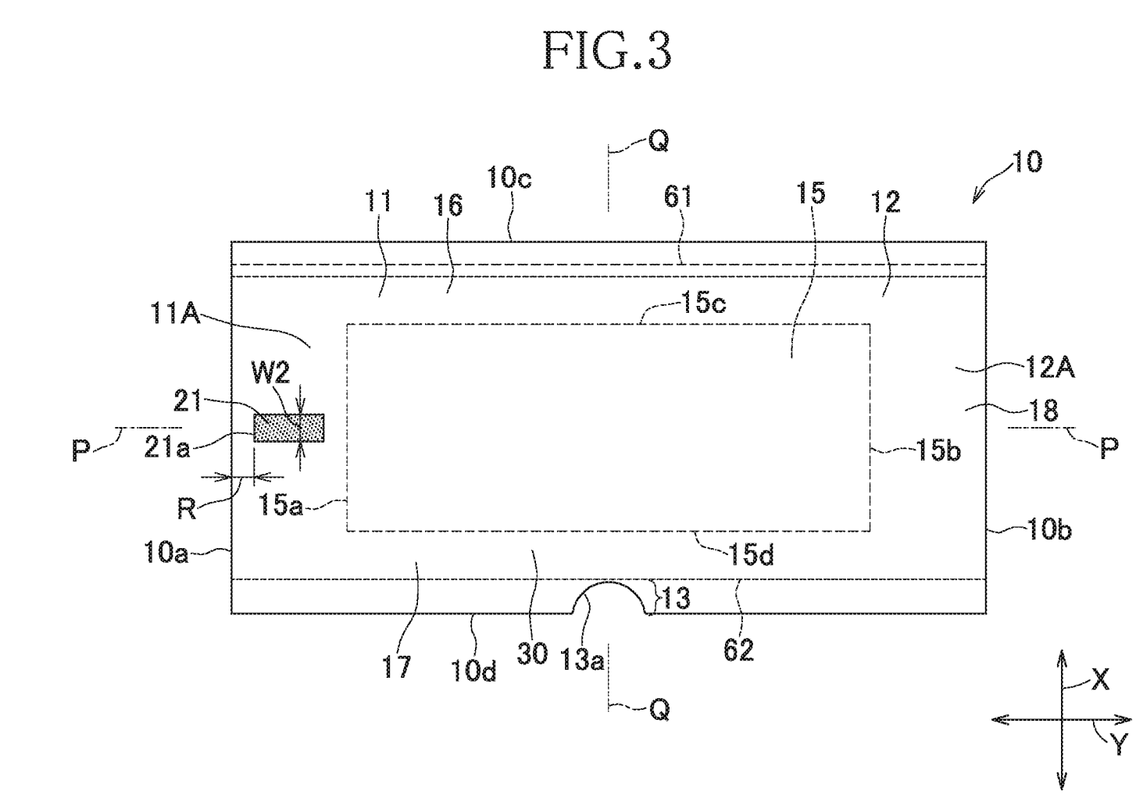
FIG. 3 is a development plan view of the absorbent article in the expanded state, as in FIG. 2, as viewed from a non-body-facing surface side.

As illustrated in FIG. 3, a first section 11 has the non-body-facing surface (outer surface) provided with an attachment 21 to be detachably attached to the second section 12. The second section 12 has the body-facing surface (or the non-body facing surface) provided with an attachment target part 22 to which the attachment 21 is attached.

Figure 2:
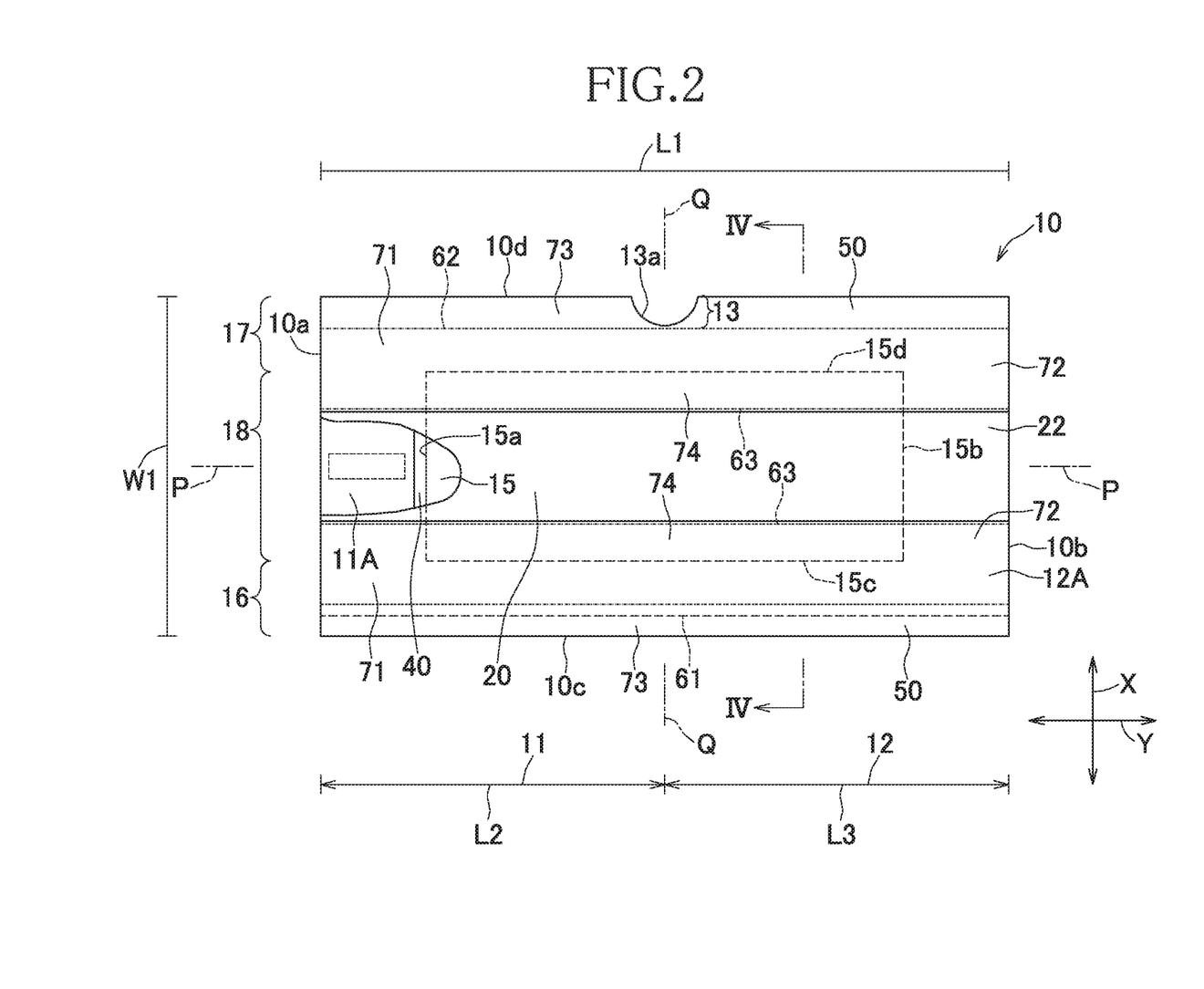
FIG. 2 is a partially cut away development plan view of the absorbent article, expanded in a longitudinal direction and a width direction, to the maximum extent allowed by elastic members (until the gather produced by compressing effect of the elastic members disappear), as viewed from a body-facing surface side.

In FIG. 2, the absorbent article 10 has a length L1, which is approximately 300 to 1000 mm, in the longitudinal direction Y and has a length W1, which is approximately 80 to 500 mm, in the width direction X. The first section 11 and the second section 12 respectively have lengths L2 and L3, which are each approximately 150 to 500 mm, in the longitudinal direction Y.

Figure 4:
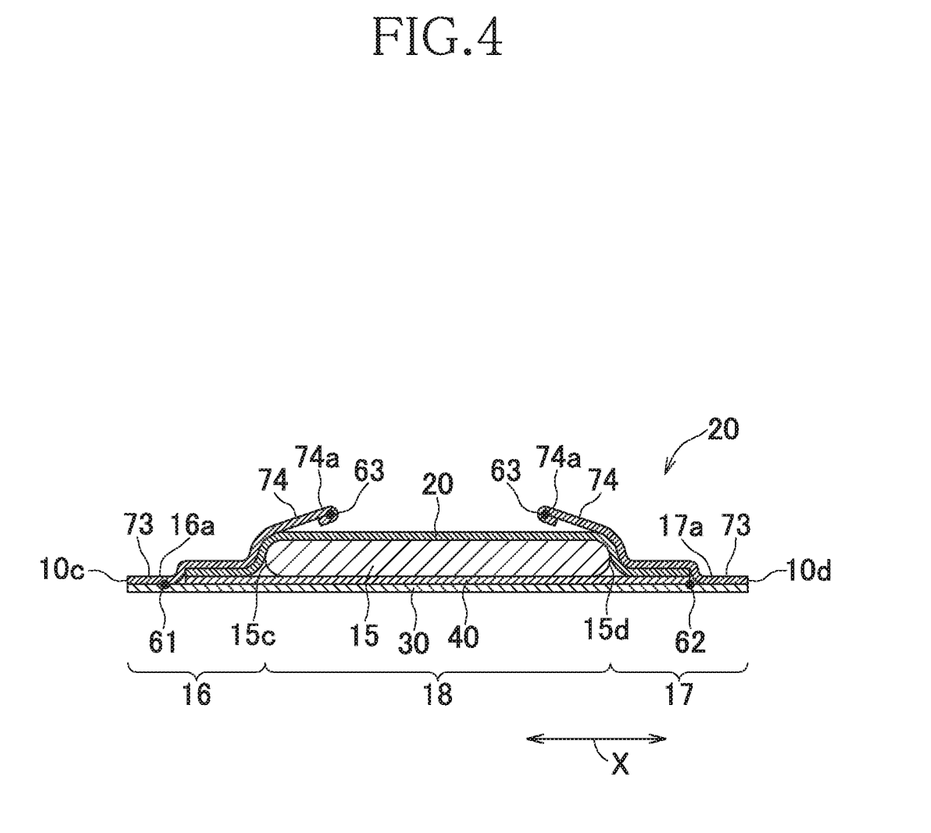
FIG. 4 is a cross-sectional view taken along line IV-IV in FIG. 2.

The absorbent article 10 further includes a liquid-permeable interior layer sheet 20, a liquid-impermeable exterior layer sheet 30, and an absorbent core 15. The liquid-permeable interior layer sheet 20 is positioned on the body-facing surface. The liquid-impermeable exterior layer sheet 30 may be made of a moisture-permeable plastic film, a fibrous nonwoven fabric, a laminate sheet including these, or the like, and is positioned on the non-body-facing surface. The absorbent core 15 is positioned in first and second sections 11 and 12 and is interposed between the interior and the exterior layer sheets 20 and 30. A leakage-barrier sheet 40 is provided between the absorbent core 15 and the exterior layer sheet 30, and may be made of a non-liquid permeable and moisture permeable plastic film. The interior and the exterior layer sheets 20 and 30 and the leakage-barrier sheet 40 extend beyond a circumference edge of the absorbent core 15. Outward extending portion of the sheets 20, 30, and 40, overlapped with each other, are adhered to each other with hotmelt adhesive applied to an interior surface(s) of at least one of the sheets facing each other.

The absorbent article 10 has the body-facing surface side (or the body-facing surface of the interior layer sheet 20) provided with a pair of cover sheets 50 extending in the longitudinal direction Y along the first and the second side edges 10c and 10d. The cover sheet 50 may be made of a fabric, a plastic film, a laminate sheet including these, or the like. The cover sheets 50 are fixed while covering the interior layer sheet 20, and are fixed to each other with hotmelt adhesive (not illustrated), via the outward extending portion of the exterior layer sheet 30, extending outward beyond the both side edges of the interior layer sheet 20 in the width direction X. As described above, the cover sheets 50 cover both side edge portions of the interior layer sheet 20, and the absorbent article 10 has both side edge portions made of liquid-impermeable sheets. Thus, urine discharged from the both side edges of the interior layer sheet 20 can be prevented from leaking out.

The absorbent core 15 has a rectangular shape contoured by both edges 15a and 15b and both side edges 15c and 15d in between these edges. The both edges 15a and 15b are opposed to each other in the longitudinal direction Y. The both side edges 15c and 15d extend in the longitudinal direction Y. The absorbent core 15 may be made of a mixture including materials known as superabsorbent polymer (SAP) particles and wood fluff pulp, and optionally including a small amount of thermoplastic fibers. The SAP is insoluble and features excellent water absorbency (capable of absorbing water in an amount that is 10 times as much as its mass or more). The absorbent core 15 is covered with a core cover sheet (not illustrated) made of nonwoven fabrics or tissue paper having hydrophilicity and liquid diffusing property. The core cover sheet is adhered to the interior layer sheet 20 and/or the leakage-barrier sheet 40 with hotmelt adhesive.

As illustrated in FIG. 2 and FIG. 3, the absorbent article 10 includes first and second side areas (both side areas) 16 and 17 and an intermediate area 18 positioned between the first and the second side areas 16 and 17 in the width direction X. The first and the second side areas 16 and 17 are positioned more on the outer side than the both side edges 15c and 15d of the absorbent core 15 in the width direction X and extend in the longitudinal direction Y. The elastic member (first elastic member) 61 is secured between the exterior layer sheet 30 and the cover sheet 50, in the first side area 16, in a contractible manner under tension. The elastic member 61 is in a string form or a strand form, and extends in the longitudinal direction Y. The first side area 16 includes a side edge 16a where an elastic portion is formed. Contracting force of the elastic member 61 is applied to the elastic portion. Thus, in a worn state, the side edge 16a may be frilled. A second elastic member 62, extending in the longitudinal direction Y, is secured to the second side area 17. With the second elastic member 62 provided on the second side area 17, the contracting force of the second elastic member 62 is applied to an elastic portion of the sided edge 17a of the second side area 17 so that the elastic portion may be frilled.

The cover sheet 50 includes both end fixed portions 71 and 72, fixed side portions (proximal portions) 73, and free portions 74. The both end fixed portions 71 and 72 are fixed to the interior layer sheet 20 respectively on the sides of the first edge 10a and the second edge 10b. The fixed side portions 73 extends in the longitudinal direction Y between the both end fixed portions 71 and 72 and is fixed to the interior layer sheet 20. The free portions 74 are positioned on inner sides (or outer sides) of the fixed side portions 73 in the width direction X. The free portions 74 have free edges 74a, in a sleeve form, formed by folding side edge portions of the cover sheet 50. Third elastic members (cuff elastic members) 63 are secured in a corresponding one of the free edges 74a in a contractible manner under tension. In the worn state of the absorbent article 10, the third elastic members 63 are stretched so that the free portions 74 may space away from the interior layer sheet 20, whereby a pair of upstanding cuffs (barrier cuffs) are formed. With the upstanding cuffs thus formed, excretion can be prevented from flowing toward the back or the legs. The free portions 74 of the cover sheet 50 extend in an inclined manner toward the inner side in the width direction X with the both end fixed portions 71 and 72 positioned in the first and the second side areas 16 and 17 and fixed to the body-facing surface of the interior layer sheet 20.

Unlike in the present embodiment, the free portions 74 of the cover sheet 50 may be fixed while extending in an inclined manner toward the outer side in the width direction X. Furthermore, at least one of the both end fixed portions 71 and 72 may not be fixed. When the both end fixed portions 71 and 72 are not fixed, the free portions 74 can entirely extend in an inclined manner toward the inner side and/or the outer side in the width direction X, and thus can be inclined in any appropriate form.

As illustrated in FIG. 2 and FIG. 3, the attachment 21 is provided in an end portion 11A of the first section 11 between the edge 15a of the absorbent core 15 and the edge 10a of the absorbent article 10, in the non-skin facing surface of the first section 11. The attachment 21 has a rectangular shape, and includes a base sheet attached to the outer surface of the cover sheet 50 and a fastening element formed of hooks of a mechanical fastener fixed to the base sheet. The attachment target part 22, to which the attachment 21 is detachably attached, is provided in an end portion 12A of the second section 12 between the edge 15b of the absorbent core 15 and the edge 10b of the absorbent article 10, in the skin facing surface of the second section 12. The attachment target part 22 may be formed of a fibrous nonwoven fabric forming the interior layer sheet. A portion where the attachment target part 22 is formed may be embossed/debossed or a non-embossed/debossed spunbound fibrous nonwoven fabric, including long fibers, may be used as the interior layer sheet. This facilitates the engagement of the hook element of the attachment 21. A target sheet including loops of the mechanical fastener may be provided in an area of the interior layer sheet 20 corresponding to the position of the attachment target part 22. The attachment 21 may be adhesive covered with a separator with a surface coated with silicon, instead of hooks, as long as the predetermined attachment strength between the attachment 21 and the attachment target part 22 can be ensured.

As illustrated in FIG. 3, the attachment 21 has a length W2, in the width direction, set to be approximately 20 mm, which is approximately 10% of the length W1 of the absorbent article 10 in the width direction X. When the length W2 of the attachment 21 in the width direction is not larger than approximately 5% of the length W1 of the absorbent article 10 in the width direction X, the attachment 21 might be unintentionally detached when the pet wearing the article change its position. When the length W2 is approximately 80% of the length W1, the end portion 11A of the first section 11 and the end portion 12A of the second section 12 are in contact with each other over a relatively large area in the width direction X. This results in a higher risk of an inner portion of the absorbent article 10 becoming damp. The edge 21a of the attachment 21 facing the edge 10a of the absorbent article 10 is positioned more on the inner side than the edge 10a of the absorbent article 10 in the longitudinal direction Y. The edges 10a and 21a has a separated portion in between with a length R of approximately 10 mm in the longitudinal direction Y. With this configuration, the separated portion can serve as a holding portion in an operation of attaching the attachment 21, while holding the end portion 11A of the first section 11, to the attachment target part 22 positioned in the end portion 12A of the second section 12. This ensures no risk of a fingertip directly touching the fastening element of the attachment 21 resulting in the skin becoming irritated.

The attachment 21 is positioned on the first axis P in the end portion 11A of the first section 11. The attachment 21 positioned on the first axis P ensures more balanced connection between the end portion 11A and the end portion 12A, compared to the case where the attachment 21 is arranged on one side of the first axis P, closer to any one of the first side area 16 and the second side area 17. Still, if the attachment 21 is not arranged on the first axis P, but is shifted on one of the sides closer to the first side area 16 or the second side area 17, the attachment 21 is preferably positioned on the side closer to the second side area 17 where the tail facing area 13 is positioned. Specifically, in a state where the attachment 21, positioned between the first axis P and the first side area 16, is attached, the first side area 16 in contact with the back of the pet 5 is pulled toward the legs 7. This improves fittability of the absorbent article 10 to the body. On the other hand, the attachment 21 positioned between the first axis P and the first side area 16 might hinder the movement of the legs 7 of the pet 5.

As illustrated in FIG. 2, the tail facing area 13 includes a substantially U-shaped notch 13a through which the tail 6 of the pet 5 is inserted. The notch 13a may be formed by partially cutting away a sheet layer including the cover sheet 50, the interior layer sheet 20, the leakage-barrier sheet 40, and the exterior layer sheet 30 layered one on top of the other in the plan view of the absorbent article 10. Furthermore, the portion cut away may have cut sections joined to each other by fusion-bonding or adhering. Furthermore, these plurality of sheets may each be partially notched in advance, so that the notch 13a is formed when the sheets are layered one on top of the other while being joined to each other. The notch 13a, having a shape protruding outward in the width direction X, may also have various other known shapes such as a linear shape, a circular shape, or a rectangular shape depending on the size or the shape of the tail 6 of the pet 5. The notch 13a, which may have any size as long as the tail 6 of the pet 5 can be inserted, may be large enough to face and thus expose the anus 9 immediately below the tail 6, so that the excretion (dropping) excreted from the anus 9 can be discharged to the outside (see FIG. 6).

The tail facing area 13 is an area facing the tail 6 of the pet 5 wearing the absorbent article 10. The tail facing area 13 may serve as a boundary area between the first and the second sections 11 and 12 that cover the buttocks of the pet 5, when the pet 5 without the tail 6 is wearing the absorbent article 10. The tail facing area 13 may not be provided with the notch 13a conforming to the shape of the tail 6. Alternatively, a substantially U-shaped cutting line defined by perforation, formed by partially cutting the absorbent article 10, may be provided instead of the notch 13a. When the tail facing area 13 is provided with the cutting line, an opening can be formed with a tongue piece, defined by the cutting line, folded outward in a state where the sheets 20 and 30 are joined or not joined. The tongue piece can be separated (ripped away) from the absorbent article 10, so as to be prevented from coming into contact with the excretion excreted from the anus 9. Furthermore, the tail facing area 13 may be provided with an opening, through which the tail can be inserted, formed by partially perforating the absorbent article 10, instead of the notch 13a or the cutting line defined by the perforation. When this perforation is formed, the absorbent article 10 can be prevented from being mispositioned during the wearing operation or while being worn, with the tail 6 inserted through the opening.

In the present embodiment, the notch 13a crosses the second axis Q and is formed to be symmetrical with respect to the second axis Q. As described above, the first and the second sections 11 and 12 are areas extending toward the first and the second edges 10a and 10b from the tail facing area 13 provided with the notch 13a. Specifically, the first and the second sections 11 and 12 are areas respectively extending toward the first and the second edges 10a and 10b from the second axis Q. Thus, the length L2 of the first section 11 in the longitudinal direction Y and the length L3 of the second section 12 in the longitudinal direction Y are substantially the same. The lengths L2 and L3 are each equal to or longer than approximately 50% of the length L1 of the absorbent article 10 in the longitudinal direction Y. Preferably, the lengths L2 and L3 of the first section 11 and the second section 12 are substantially the same, so that an amount of absorbed urine, flowed toward a floor surface 4 (lower side), can be substantially the same between the case where the pet 5 has a right side in contact with the floor surface 4 and the case where the pet has a left side in contact with the floor surface 4. The notch 13a may be shifted toward the first edge 10a or the second edge 10b instead of crossing the second axis Q. In such a configuration, the first and the second sections 11 and 12 are defined based on the center position of the tail facing area 13 (or the notch 13a) in the length direction. Thus, one of the length L2 of the first section 11 and the length L3 of the second section 12 may be larger than the other. The lengths L2 and L3 may be within a range between approximately 40% to 60% of the length L1.

Figure 1:
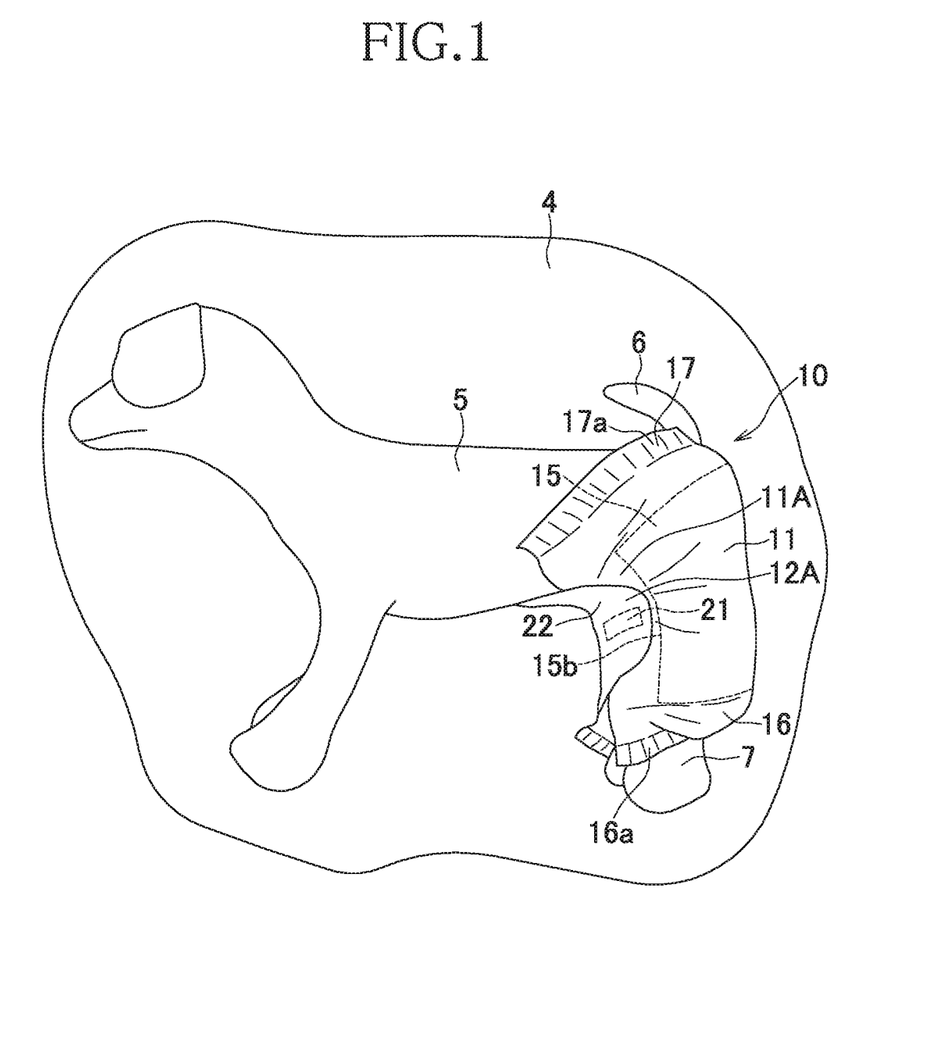
FIG. 1 is a diagram illustrating a pet, wearing an absorbent article for pet animals according to a first embodiment of the present invention, is lying on one side.
Figure 5:
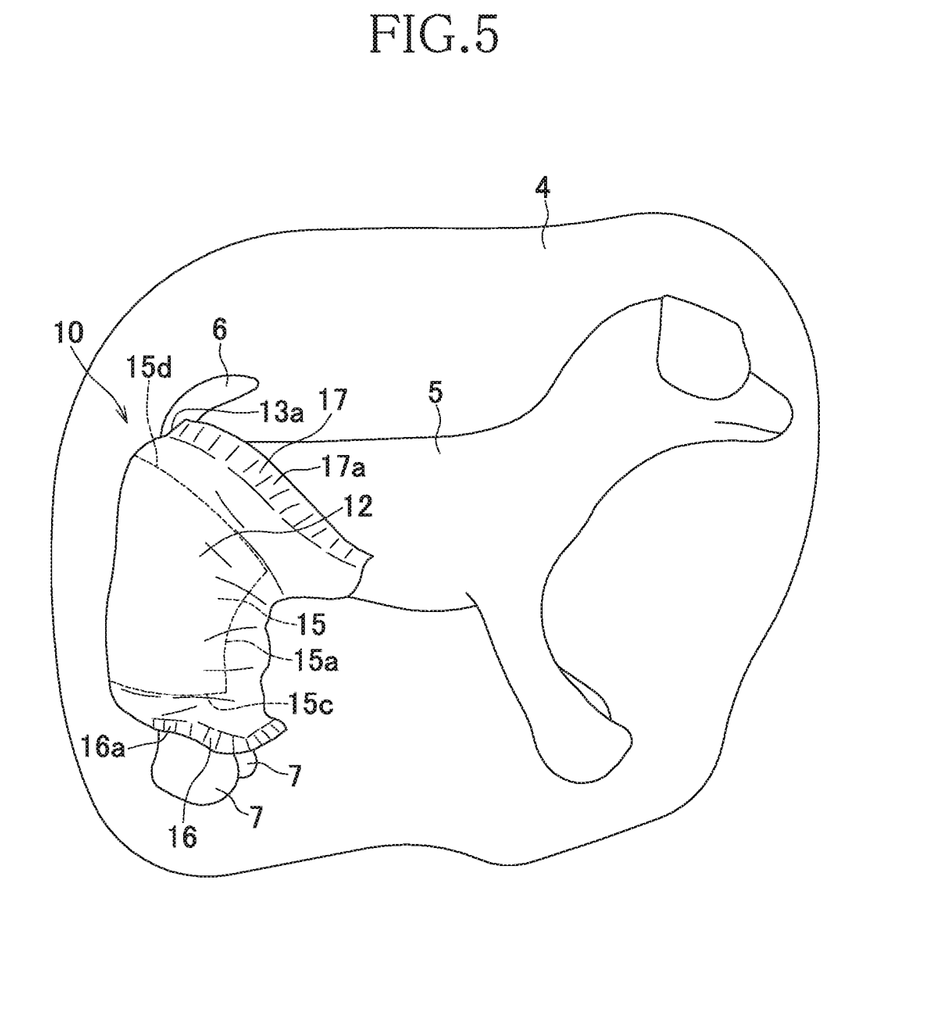
FIG. 5 is a diagram illustrating the pet lying on a side opposite to that in FIG. 1.
Figure 6:
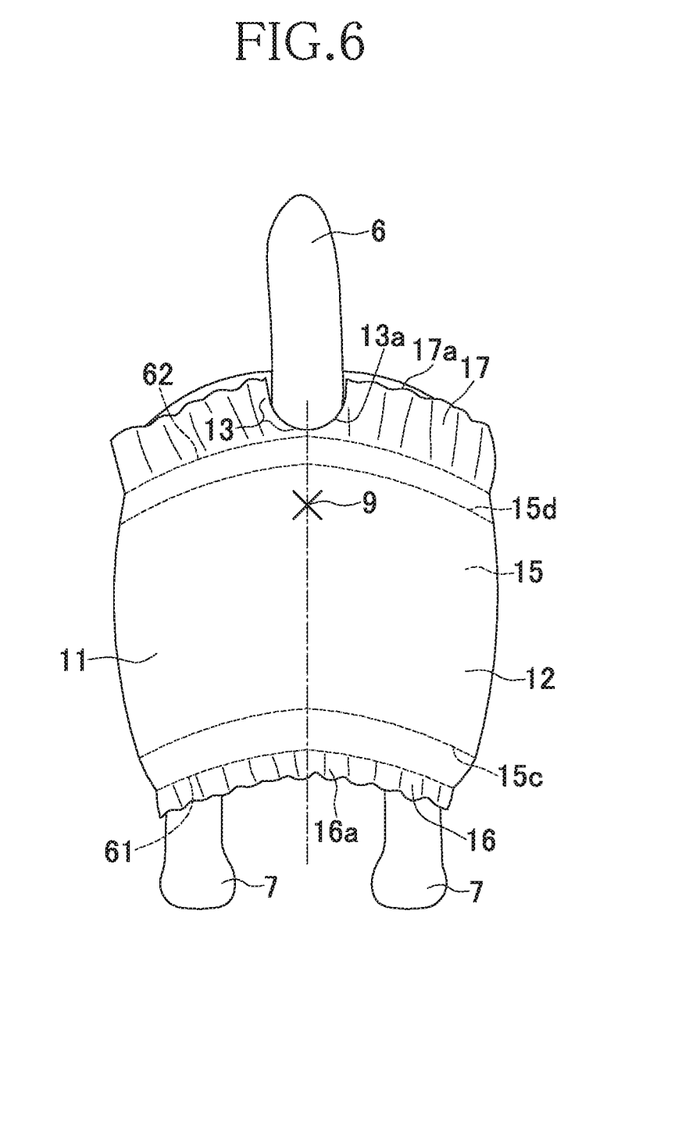
FIG. 6 is a rear view of the pet wearing the absorbent article, as viewed from a rear side.
Figure 7:
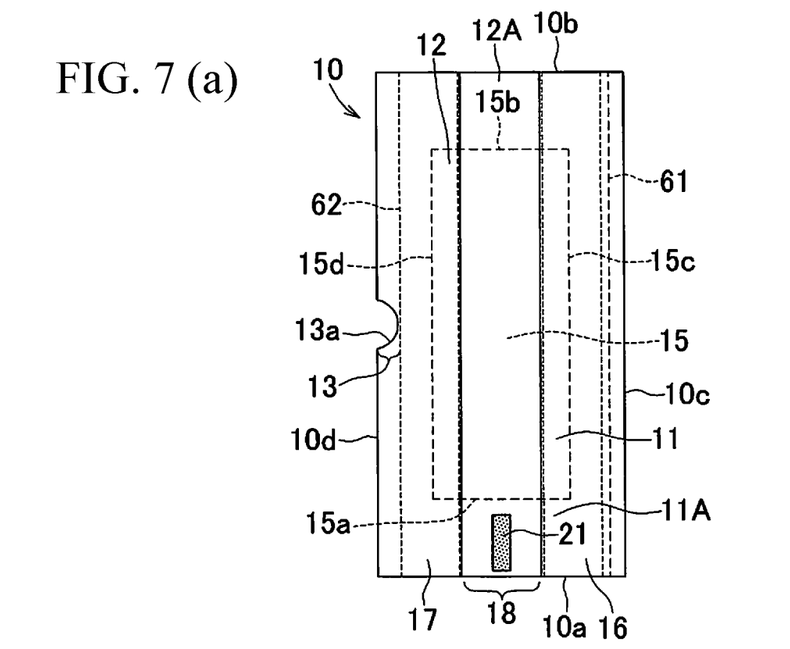
FIG. 7(a) is a development plan view of an absorbent article according to one exemplary modification, under a condition similar to that in FIG. 2.
FIG. 7(b) is a diagram illustrating the absorbent article according to the exemplary modification in a used state.

As illustrated in FIG. 1, FIG. 5, and FIG. 6, the absorbent article 10 is put on a bedridden pet 5 with the tail 6 placed in the notch 13a positioned in the tail facing area 13 while placing the first section 11 (or the second section 12) placed on one of the buttocks of the pet 5 that is not in contact with the floor surface 4. Next, the body of the pet is lifted and the second section 12 (or the first section 11) is placed on the other one of the buttocks that has been in contact with the floor surface 4. Then, the end portion 12A of the second section 12 is held and pulled toward the first section 11. Then, the attachment target part 22, positioned on the skin facing surface of the end portion 12A, is pressed against and attached to the attachment 21 positioned on the non-skin facing surface of the end portion 11A of the first section 11.

A relatively old (10 years old or older) pet 5 cannot stay lying on its stomach when resting, and is bedridden with half of its body in contact with the floor surface 4. When the pet 5 thus lying on its side urinates, the urine excreted might spread on the floor surface 4 toward the back side of the pet 5 and/or toward the rear side of the pet 5. An absorbent article generally used as a diaper for a male pet includes a diaper worn with a ventral area and a dorsal area connected to each other via an engagement means and a diaper worn with both end portions connected to each other while being encircled around the waist of the pet 5. Such diapers are designed for urination by the pet taking a standing/sitting position or lying down. Specifically, an excretory opening is covered with an absorbent core, extending in a longitudinal direction (front and rear direction) of the body. Thus, the urine is quickly absorbed and while spreading in the front and rear direction. With this configuration, when the pet is lying on its side, an area of the absorbent core positioned on a portion in contact with the floor surface is relatively small. Thus, bodily fluid flowing to spread toward the back side and the rear side of the pet might be failed to be sufficiently absorbed. As a result, the urine might leak out from the absorbent article. These absorbent articles have closed inner spaces for preventing the excretion from leaking. Thus, urination is likely to result in the inner space becoming damp. Furthermore, when the pet is lying on its side for a relatively long period of time so that a part of its body may be pressured, a bedsore might occur or might be worsened. An absorbent sheet may be laid on the floor surface without making the pet wear the absorbent article so that bedsore can be prevented from occurring due to the inner portion of the absorbent article becoming damp as described above. However, this might result in the urine spreading on the absorbent sheet soiling a large part of the body.

The absorbent article 10 according to the present embodiment entirely covers one of the right and left sides of the lower body that is in contact with the floor surface 4 with one of the first and the second sections 11 and 12. The absorbent core 15 with a relatively large area is positioned on the first and the second sections 11 and 12. Thus, a large amount of urine excreted from the anus 9 can be quickly absorbed, and can be prevented from leaking out from the absorbent article 10.

To prevent the pet 5 from having a bedsore on a part of its body, the supporter needs to change the side of the pet 5 in contact with the floor surface (flip the pet upside down). For example, as illustrated in FIG. 1, when a predetermined period of time (for example, two hours) elapses after the second section 12 of the absorbent article 10 has been brought into contact with the floor surface 4, the supporter inserts one of his or her hands between the floor surface 4 and the second section 12 to hold the second section 12 and holds the first section 11 with the other hand to press the first section 11 against the buttock. Then, the supporter lifts and flips the pet 5 while the absorbent article 10 is placed on the buttocks. Then, the first section 11 is brought into contact with the floor surface 4, whereby the side of the pet in contact with the floor surface 4 is switched. Thus, the bedsore can be prevented.

The bedridden pet 5 in a relatively healthy condition might relatively largely move its legs. This results in the first and/or the second sections 11 and/or 12 partially or entirely separating from the body, if the first and the second sections 11 and 12 are not connected to each other. Thus, the bodily fluid might be failed to be absorbed by the absorbent core 15. The absorbent article 10 according to the present embodiment has the first and the second sections 11 and 12 provided with the attachment 21 and the attachment target part 22 to be partially in contact with each other. Thus, the first and the second sections 11 and 12 are not separated from the body, even when the pet 5 largely moves its legs. As described above, the first section 11 and the second section 12 of the absorbent article 10 are partially in contact with each other via the attachment 21 and the attachment target part 22, and thus are not in contact with each other entirely over the width direction. Thus, the abdominal portion of the pet is not oppressed, and the inner portion of the article is not closed but is in an open state. Thus, the inner portion can be prevented from becoming damp, whereby the bedsore can be prevented from occurring or worsening.

The absorbent article 10 according to the present embodiment has the elastic portion, as a result of the contracting action of the first elastic member, positioned in the side edge 16a of the first side area 16, and the elastic portion, as a result of the contracting action of the second elastic member, positioned in the side edge 17a of the second side area 17. The elastic portions ensure excellent fittability to the waist and legs of the pet 5. Thus, the elastic portions may function as means for achieving better fittability of the absorbent article 10 to the body, in addition to the connection between the attachment 21 and the attachment target part 22.

Referring back to FIG. 1 and FIG. 5, the side edge 17a of the second side area 17 extends diagonally downward relative to the body (waist) of the pet in side view, in a state where the attachment 21 of the first section 11 is attached to the attachment target part 22 of the second section 12. With the side edge 17a diagonally extending relative to the body in the worn state, the back side can be exposed unlike in the configuration where the side edge 17a extends along the body inside view. Thus, the inner portion of the absorbent article 10 can be prevented from becoming damp.

<First Modification>

FIG. 7(a) is a development plan view of the absorbent article 10 according to one exemplary modification in an open state as in FIG. 2. FIG. 7(b) illustrates the absorbent article 10 according to one exemplary modification in a used state.

In this modification, the attachment 21 is positioned on the skin facing surface of the first section 11, and the attachment target part 22 is positioned on the skin facing surface (or the non-skin facing surface) of the second section 12. Specifically, in this configuration where the attachment 21 positioned on the skin facing surface of the first section 11, as illustrated in FIG. 7(b), the end portion 11A of the first section 11 and the end portion 12A of the second section 12 can be connected to each other while facing each other, with the attachment 21 attached to the attachment target part 22 formed as a part of the interior layer sheet 20. Alternatively, the attachment 21 may be positioned on the non-skin facing surface of the end portion 12A of the second section 12. Thus, the end portion 11A of the first section 11 and the end portion 12A of the second section 12 may be connected to each other while overlapping with each other in the front and rear direction in the worn state, with the attachment 21 attached to the attachment target part 22 formed as apart of the exterior layer sheet 30.

<Second Modification>

Figure 8:
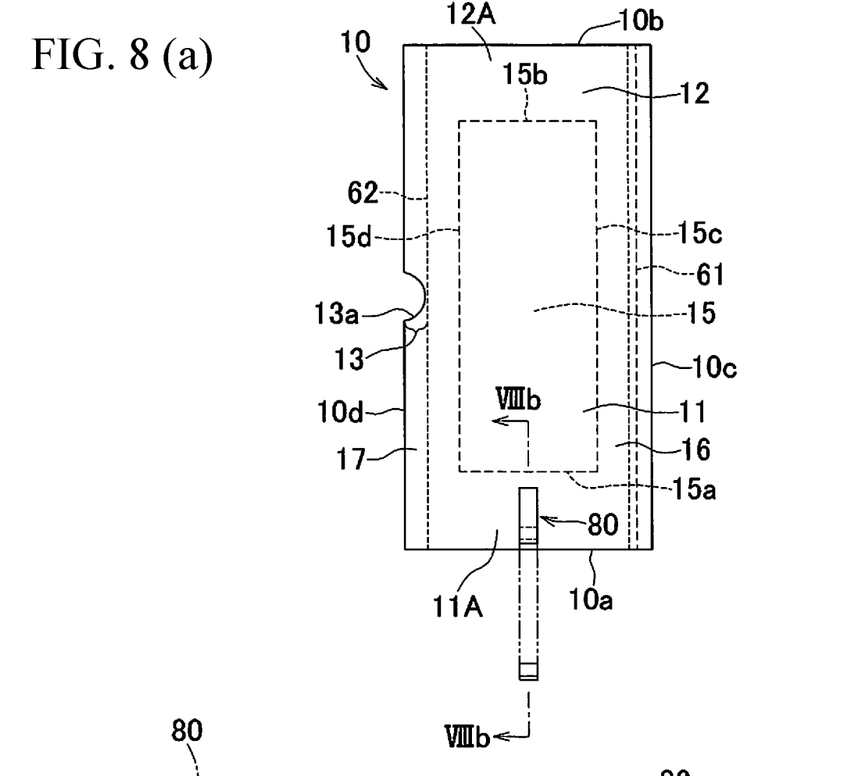
FIG. 8(a) is a development plan view of an absorbent article according to another exemplary modification, under a condition similar to that in FIG. 3.
FIG. 8(b) is a cross-sectional view taken along line VIII(b)-VIII(b) in FIG. 8(a).

FIG. 8(a) is a plan view illustrating the absorbent article 10 according to another modification, in an open state as in FIG. 3. FIG. 8(b) is a cross-sectional view taken along line VIII(b)-VIII(b) in FIG. 8.

As illustrated in FIGS. 8(a) and 8(b), in the present modification, a tape fastener 80 is provided on the non-skin facing surface of the end portion 11A of the first section 11. The tape fastener 80 is made of one piece of tape material folded to have a Z-shaped cross section, and includes a fixed portion 81 fixed to the first section 11 via a joint area 79 formed by applying hotmelt adhesive, and a free portion 82 detachably attached to the fixed portion 81 while being in a folded state. The free portion 82 of the tape fastener 80 includes a first free portion 82A that continues from the fixed portion 81 and faces the fixed portion 81 in a thickness direction Z of the tape fastener 80 by being folded relative to the fixed portion 81 and a second free portion 82B continuing from the first free portion 82A and faces the first free portion 82A in the thickness direction Z. The tape fastener 80 further includes a first folded portion 83A and a second folded portion 83B positioned more on the outer side than the first folded portion 83A in the width direction X. The fixed portion 81 and the first and the second free portions 82A and 82B, in a layered state, are detachably attached each other via detachably attaching portions 85 and 86 positioned on the first and the second folded portions 83A and 83B. The free portion 82 further includes a holding portion 87 extending outward from the detachably attaching portion 85, positioned on the first folded portion 83A, in the width direction X. The second free portion 82B, between the detachably attaching portions 85 and 86, has an inner surface provided with the attachment portion 88. The attachment portion 88 is formed of a hook sheet including the hook element of the mechanical fastener. The hook sheet is attached to the tape material. The detachably attaching portions 85 and 86 may be formed by performing known pressing processing and heat pressing processing. For example, known embossing/debossing processing or supersonic processing may be employed.

The absorbent article 10 with the attachment 88 provided to the free portion 82 of the tape fastener 80 is put on the pet 5 as follows. Specifically, a user holds and pulls the holding portion 87 toward the outer side in the width direction X, so that the detachably attaching portions 85 and 86 are detached from each other. Thus, the tape fastener 80 is opened. Then, the user presses and attaches the attachment 88 to the attachment target part 22 positioned on the non-skin facing surface of the second section 12 while holding the holding portion 87. When the absorbent article 10 is worn on a pet that is relatively large around the waist, end portions of the first section 11 and the second section 12 do not overlap with each other or overlap with each other only in a relatively small area. Here, with the attachment 88 positioned in the free portion 82 of the tape fastener 80, the first section 11 and the second section 12 can be stably attached to each other by extending in the tape fastener 80. An edge 79a of a joint area 79 of the tape fastener 80 and an edge 10a of the absorbent article 10 are separated from each other, in the longitudinal direction Y, so that the body is not stimulated due to stiffness of the tape fastener 80. With the edge 79a and the edge 10a separated from each other, the separated portion might be lifted from the body. However, in a state where the attachment portion 88 is attached to the attachment target part 22 with the tape fastener 80 extended, the separated portion is pressed against the body and thus can be prevented from lifting from the body.

The tape fastener 80 may be provided on the skin facing surface instead of the non-skin facing surface of the first section 11. In such a configuration, for example, a tape fastener arranged to be in a Y shape or an I shape in plan view, instead of the Z cross-sectional shape as in the modification, may be employed. The tape fastener 80 may be used as a tape for maintaining a rolled state, when the absorbent article 10 that has been used is discarded in a rolled form.

The components of the absorbent article 10 are not limited to those described in this description, and known materials generally used in this technical field may be used, unless otherwise noted. The terms used in this specification, such as "first", "second", and "third", are used merely for the distinction between similar elements, positions, or the like.

REFERENCE SIGNS LIST

5 pet animal
6 tail
10 absorbent article for pet animal
10a first edge
10b second edge
11 first section
12 second section
13 tail facing area
15 absorbent core
16 first side area (one or the other side area)
17 second side area (one or the other side area)
20 interior layer sheet
21 attachment
22 attachment target part
30 exterior layer sheet
61 first elastic member
62 second elastic member
63 third elastic member
X width direction
Y longitudinal direction

The invention claimed is:

1. An absorbent article for pet animals, the absorbent article having a longitudinal direction and a width direction crossing each other, the absorbent article comprising:
   a body-facing surface and a non-body-facing surface opposite to each other;
   a first edge and a second edge opposite to each other in the longitudinal direction;
   a tail facing area configured to face a tail of a pet;
   a first section extending from the tail facing area toward the first edge and configured to cover one of buttocks of the pet;
   a second section extending from the tail facing area toward the second edge and configured to cover another one of the buttocks of the pet;
   an absorbent core positioned between the first section and the second section; and
   an attachment positioned on the first section and configured to be attached to an attachment target part on the second section,
   wherein
   the tail facing area includes a notch through which the tail of the pet is to be inserted,
   the absorbent article has a first axis bisecting a length of the absorbent article in the width direction,
   the absorbent article further includes first and second side areas provided more on an outer side than both side edges of the absorbent core in the width direction and extending in the longitudinal direction, and
   the tail facing area is positioned on the first side area.

* * * * *